United States Patent [19]

Schasteen et al.

[11] Patent Number: 5,591,431
[45] Date of Patent: Jan. 7, 1997

[54] ENHANCEMENT OF CLOT LYSIS

[75] Inventors: Charles S. Schasteen, University City; Kathleen C. Day, Kirkwood; Rory F. Finn, Ballwin, all of Mo.

[73] Assignee: G.D. Searle & Co., Chicago, Ill.

[21] Appl. No.: 495,008

[22] Filed: Mar. 9, 1990

[51] Int. Cl.⁶ .......................... A61K 37/02; A61K 37/54
[52] U.S. Cl. .................................... 424/94.64; 514/13
[58] Field of Search .................... 424/94, 94.64; 514/13; 530/393; 930/250; 435/212, 219, 226

[56] References Cited

U.S. PATENT DOCUMENTS

| | | | |
|---|---|---|---|
| 4,340,589 | 7/1982 | Uemura et al. | 530/393 |
| 4,632,981 | 12/1986 | Bock et al. | 530/393 |
| 4,661,471 | 4/1987 | Hawiger et al. | 930/250 |
| 4,760,130 | 7/1988 | Thompson et al. | 930/250 |
| 4,790,988 | 12/1988 | Mehta et al. | 424/94.64 |
| 4,861,865 | 8/1989 | Horton | 530/326 |

Primary Examiner—Jacqueline M. Stone
Attorney, Agent, or Firm—Dennis A. Bennett

[57] ABSTRACT

The invention discloses methods and compositions for increasing clot lysis in the presence of exogenous tissue plasminogen activator.

14 Claims, 5 Drawing Sheets

ENHANCEMENT OF CLOT LYSIS

BACKGROUND OF THE INVENTION

The invention relates to methods of increasing tissue plasminogen activator (tPA) mediated clot lysis and compositions for achieving increased tPA mediated clot lysis.

It is well known that surgery, delivery, major trauma and infectious diseases are associated with an increased risk of thrombosis, i.e., formation of intravascular blood clots. One may endeavor to prevent such clots by administering anticoagulants, such as heparin, coumarin derivatives, snake venom components or indanediol. In the case where thrombosis has occurred, however, use may be made of thrombolytic agents whose function is to remove the resulting blood clots from the blood vessels by dissolution (lysis).

For a better understanding of the present invention, it is noted that blood clots are composed of fibrin which has been formed from fibrinogen under action of the enzyme thrombin. The process of blood clotting (thrombosis) involves a complex system of interacting enzyme factors, each of which is converted by other enzymes from an inactive to an active form. As a result of the overall activity of this system, protein fibers called fibrin become enmeshed in a mass which curtails blood flow at the point of the thrombosis. Where such thrombosis occurs at the site of a cut, the effect is the protective reduction of blood loss through bleeding. But where such thrombosis occurs in a uncontrolled manner in major arteries supplying the lungs, brain or other vital organs, the result may be paralysis, loss of neural function, or death, unless the fibrin clot can be removed expeditiously. Examples of thrombosis in major arteries of life threatening magnitudes include cerebral thrombosis, renal thrombosis, ophthalmic artery thrombosis and thrombosis of a coronary artery. The inability to remove the fibrin clot in major arteries is the most frequent cause of mortality in the developed world.

Mammalian plasma, however, does contain an enzymatic system capable of dissolving the fibrin in blood clots. One component of the enzymatic (fibrinolytic) system consists of the enzymes referred to as plasminogen activators which convert plasminogen (an inactive proenzyme form of plasmin) into the proteolytic enzyme plasmin. Plasmin then degrades the fibrin network of the large, insoluble fibrin mass (clots) to form soluble components.

A plasminogen activator is naturally present in normal blood or is released into the blood so that the circulating blood contains, in principle, all ingredients necessary to degrade and remove an intravascular blood clot once it has been formed. One plasminogen activator, called tissue plasminogen activator (tPA), is known to exist in most human tissues. Although immunologically similar, tPA originates from different tissues and may differ from each other with respect to their molecular properties. Characteristics of tPA include greatly enhanced fibrinolytic action in the presence of fibrin, as well as high affinity for fibrin. Because of their high affinity for fibrin, the action of tPA is confined to the locality of the clot thereby reducing significantly the danger of uncontrolled hemorrhage.

In reality, however, it appears that the thrombolytic potential of the body is frequently insufficient for this purpose which means that an adequate removal of intravascular thrombi may require the use of exogenously administered thrombolytic agents. Therefore, in cases where the thrombolytic potential of the body is insufficient to remove intravascular thrombi formed, it is necessary to use exogenously administered thrombolytic agents.

It has now been discovered that a 22 amino acid peptide which was shown to have protease inhibitory activity toward certain complement proteases (G. I. Glover et al., *Molec. Immunol.* 25:1261 (1988) and C. S. Schasteen et al. *Molec. Immunol.* 25:1269 (1988)) enhances tPA mediated clot lysis. The peptide corresponds to residues 382 to 403 of Antithrombin III (ATIII) and is a member of a series of peptide serine protease inhibitors that are homologous to regions of naturally occurring serum serine protease inhibitors. The methods and compositions provided by the present invention provide a means to exogenously administer thrombolytic agents which enhance tPA mediated clot lysis, thereby helping to remove the thrombi.

SUMMARY OF THE INVENTION

The invention comprises a method for enhancing clot lysis in the presence of exogenous tissue plasminogen activator (tPA). In addition, the invention comprises compositions for enhancing clot lysis. A preferred composition comprises a 22 amino acid peptide and tPA. Not only do the methods and compositions of the invention enhance clot lysis, they also leave unaltered the tPA fibrin specificity and tPA half-life.

DESCRIPTION OF THE INVENTION

Figure 1:
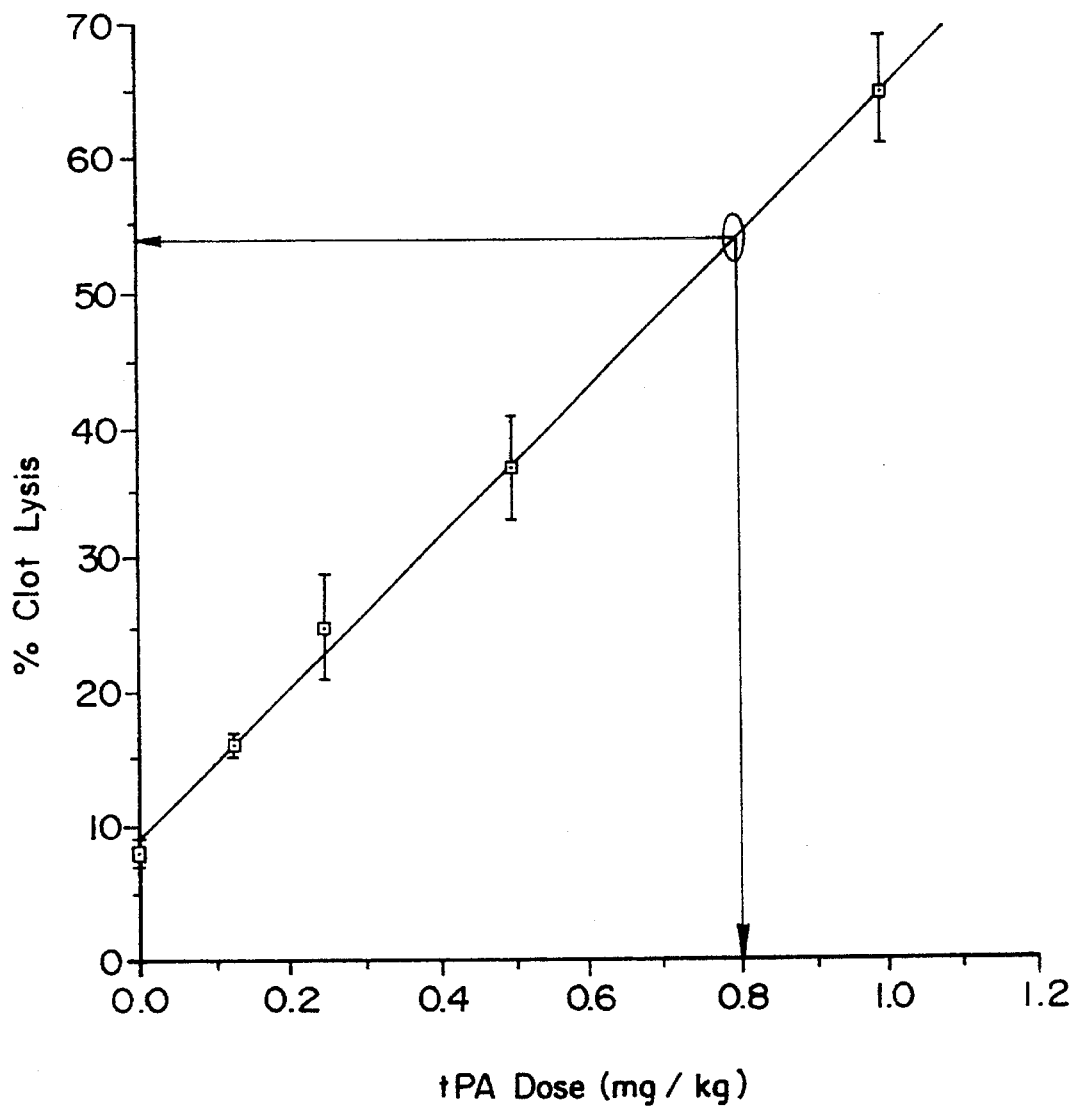
FIG. 1—tPA Standard Clot Lysis Curve 1 for Model I. Data represented as Clot Lysis Mean +/− Standard error of the mean (SEM). Number of animals for each data point (N=3)

The present invention comprises a method for enhancing clot lysis in the presence of exogenous tissue plasminogen activator (tPA) which method comprises administering a 22 amino acid peptide (hereinafter referred to as the enhancer peptide) which has the following amino acid sequence:

Ala-Gly-Arg-Ser-Leu-Asn-Pro-Asn-Arg-Val-Thr-Phe-Lys-Ala-Asn-Arg-Pro-Phe-Leu-Val-Phe-Ile.

The enhancer peptide exhibits the ability to enhance clot lysis in the presence of exogenous tPA. Not only does the enhancer peptide enhance clot lysis but it does not affect tPA fibrin specificity and tPA half-life. Another embodiment of the invention comprises compositions for enhancing clot lysis.

For purposes of the description and claims, the nomenclature referenced in *The Journal of Biological Chemistry*, 260:14 (1983) as set forth herein will be used to identify the naturally occurring amino acids: alanine (Ala;A), asparagine (Asn:N), aspartic acid (Asp;D), arginine (Arg;R), cysteine (Cys;C), glutamic acid (glu;E), glutamine (Gln;Q), glycine (Gly;G), histidine (His,H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

All peptide structures represented herein are shown in conventional format wherein the amino group at the N-terminus is to the left and the carboxyl group at the C-terminus is to the right. Unless noted otherwise, all amino acids are L-amino acids.

Two independent studies were performed using the rabbit jugular vein thrombolysis model described in D. Collen et al., *J. Clin. Invest.* 71:368 (1983), with minor modifications. The enhancer peptide was administered during clot formation prior to tPA administration in one set of experiments with the rabbit jugular vein thrombolysis model. The enhancer peptide produced a five-fold increase in the clot lysis obtained from infusion of 0.125 mg tPA/kg, which corresponds to the lysis observed by a six-fold increase in tPA dose.

In a second experiment the enhancer peptide was administered with tPA. Coinfusion of 0.125 mg tPA/kg and enhancer peptide at two separate doses (1.85 mg/kg and 18.5 mg/kg) resulted in a five-fold increase in clot lysis, which is equivalent to the lysis resulting from infusion of a three-fold higher tPA dose.

In addition to the enhanced clot lysis observed by administering the enhancer peptide, the tPA half-life, as measured by tPA antigen levels in the blood, was not altered. Likewise, clot specificity, as measured by fibrinogen and $\alpha$-2-antiplasmin levels, was not altered.

The enhancer peptide is administered in conjunction with tPA, for example, between about one (1) minute and about thirty (30) minutes prior to the administration of tPA, or between about one (1) minute and about thirty (30) minutes after the administration of tPA. Preferably the enhancer peptide is co-administered with exogenous tPA. Suitable ranges of tPA are from about 10 mg to about 150 mg per patient with about 50 mg to about 100 mg preferred. Typically, about 10% of the total dose is administered during the first about five minutes with the remaining 90% of the total dose administered during the two hour period following the initial 10% dose. Alternatively, an amount of tPA larger than 10% of the total dose can be administered, for example about 10–50%, during the first five minutes, with the remainder of the total dose administered during the period following the initial dose, about two hours. Effective dose ranges of the enhancer peptide range from about 100 mg to about 2,250 mg per patient with a range of about 250 mg to 1,500 mg preferred. Therefore, when administering the enhancer peptide with tPA, dosage of tPA will be adjusted in accordance with dosage of enhancer peptide (due to the enhancing effect of the enhancer peptide with tPA).

The enhancer peptide can also be administered as a composition comprising tPA and enhancer peptide. The enhancer peptide can be added to tPA in effective amounts ranging from about 20:1 by weight excess enhancer peptide to about 1:5 by weight excess tPA. A range of about 15:1 by weight excess enhancer peptide to about 1:1 by weight is preferred.

The quantity of material administered will depend upon the physical characteristics of the recipient, the amount of fibrinolysis required, the speed with which lysis is required, the seriousness of the thromboembolic condition, and the position and size of the clot. The precise dose to be employed and mode of administration will be decided according to the circumstances. The amount to be administered must be a lysis enhancing amount, defined as an amount which is medically beneficial (i.e. sufficient to eliminate the clot or reduce its size) but does not present serious side effects, such as excessive bleeding, which outweigh the advantages of the use.

The present invention provides a pharmaceutical composition comprising the enhancer peptide and tPA, usually in combination with pharmaceutically acceptable salts and pharmaceutically acceptable carriers. The term "pharmaceutically acceptable salt" refers to those acid addition salts or metal complexes of the peptide which do not significantly or adversely affect the therapeutic properties (e.g. efficacy, toxicity, etc.)of the peptide. The term "pharmaceutically acceptable carrier" refers to those solid and liquid carriers which do not significantly or adversely affect the therapeutic properties of the peptide. Non toxic pharmaceutically acceptable salts that may be used and still maintain biological activity of the parent compound include those formed with hydrochloric acid, nitric acid, cobalt, nickel, phosphoric acid, tartaric acid, zinc, and zinc tannate. Carriers may include sterile water, saline, and buffered saline including buffers like phosphate or acetate, sodium chloride or sucrose as pressure adjusting agents, and antioxidants such as ascorbic acid, or any acceptable combinations thereof. Intravenous administration of the peptides in solution with normal physiologic saline is illustrative. Examples of suitable formulations for use with the enhancer peptide or the composition comprising the enhancer peptide and tPA, in pharmaceutically acceptable diluents or carriers in therapeutic dosage form can be prepared by reference to general texts in the pharmaceutical field, such as *Remington's Pharmaceutical Sciences*, Ed. Arthur Osol, 16th ed., 1980, Mack Publishing Co., Easton, Pa. The enhancer peptide may be administered as free peptide or pharmaceutically acceptable salts thereof. The peptide will normally be administered as a pharmaceutical composition which, in most cases, will comprise the peptide and/or pharmaceutical salts thereof with a pharmaceutically acceptable carrier.

The compositions according to the invention may be formulated in accordance with routine procedures as pharmaceutical compositions adapted for intravenous, subcutaneous and intranasal administration to human beings. The composition will be suitable for parenteral administration, including intravenous or intraarterial injection or infusion. The compositions can even be administered as a bolus, for example, comprising tPA and the enhancer peptide. The preferable route of administration is parenteral with intravenous preferred.

Typically, compositions for intravenous administration are solutions of the enhancer peptide or composition comprising the enhancer peptide and tPA in sterile isotonic aqueous buffer. Where necessary the compositions may also include a solubilizing agent to keep the compositions in solution and a local anaesthetic such as lidocaine to ease pain at the site of injection. Generally, the compositions will be supplied in unit dosage form, for example as a dry powder or water free concentrate in a hermetically sealed container such as an ampoule or sachette indicating the quantity of fibrinolytic enzyme in activity units. Where the compositions are to be administered by infusion, it will be dispensed with an infusion bottle containing sterile pharmaceutical grade 'Water for Injection' or saline. Where the compositions are to be administered by injection, they are dispensed with an ampoule of 'Water Injection' or saline for injection. The injectable or infusable compositions will be made by mixing the ingredients prior to administration.

The peptide may be administered to human patients in an effective dose and will have a potent and effective thrombolytic effect. Use of the enhancer peptide allows for less tPA to be administered, thereby decreasing the potential for tPA-induced side effects. Therefore, the peptide may be used for curing acute and chronic thromboembolic occlusions of different vascular beds such as encountered in deep vein thrombosis, cerebral thrombosis, renal thrombosis, ophthalmic artery thrombosis, and thrombosis of a coronary artery.

The following examples illustrate the specific embodiments of the invention described herein. As would be apparent to skilled artisans, various changes and modifications are possible and are contemplated within the scope of the invention described.

EXAMPLES

The enhancer peptide of this invention having the formula:

Ala-Gly-Arg-Ser-Leu-Asn-Pro-Asn-Arg-Val-Thr-Phe-Lys-Ala-Asn-Arg-Pro-Phe-Leu-Val-Phe-Ile and control peptides are synthesized by the solid phase method (Stewart, J. M. and Young, J. D., *Solid Phase Peptide Synthesis*, 2nd Edition, Rockford, Ill.: Pierce Chemical Company, 1984) and the sequences confirmed by amino acid composition and sequence analysis.

EXAMPLE 1

Antiplasmin levels were monitored by the antiplasmin assay (Helena Labs, Beaumont, Tex.). This assay measures inhibition of plasmin cleavage of a chromogenic substrate S2251 (H-D Valyl-Leucyl-L-Lysine-p-nitroanilide dihydrochloride) obtained from Helena Labs. A typical reaction mixture contains 215 μL of 50 mM Tris buffer pH 7.4, 110 mM NaCl, 5 μL rabbit plasma, 15 μL plasmin (1 unit), and 15 μL of substrate S2251 (3.5 mM stock) in a total reaction volume of 250 μL. The generation of p-nitroaniline product is monitored at 405 nM.

Fibrinogen concentration in dilute plasma is inversely proportional to the thrombin clotting of the plasma (S. Borgstrom, *Acta Chir. Scand.* 90:419 (1945); A. Clauss, *Acta Haemat*, 17:273 (1957); K. Jacobson, *Scand. J. Clin. Lab. Med.* 7:7 (1955). Plasma was diluted 1:10 and 200 μL of this solution added to 100 μL (10 units) of bovine thrombin. Clotting time was measured on a clinical fibrometer, and fibrinogen levels determined as mg/dL plasma.

Samples of rabbit plasma were assayed by a commercial ELISA assay from American Diagnostic Inc. (ADI), New York, N.Y. Several modifications are made to the ADI protocol, which include using 10 μL of untreated plasma sample to minimize background and spiking the standard curve with 10 μL rabbit plasma to equalize any salt effect that might result. The assay was standardized with mouse C127 cell tPA (Invitron, St. Louis, Mo.).

Figure 2:
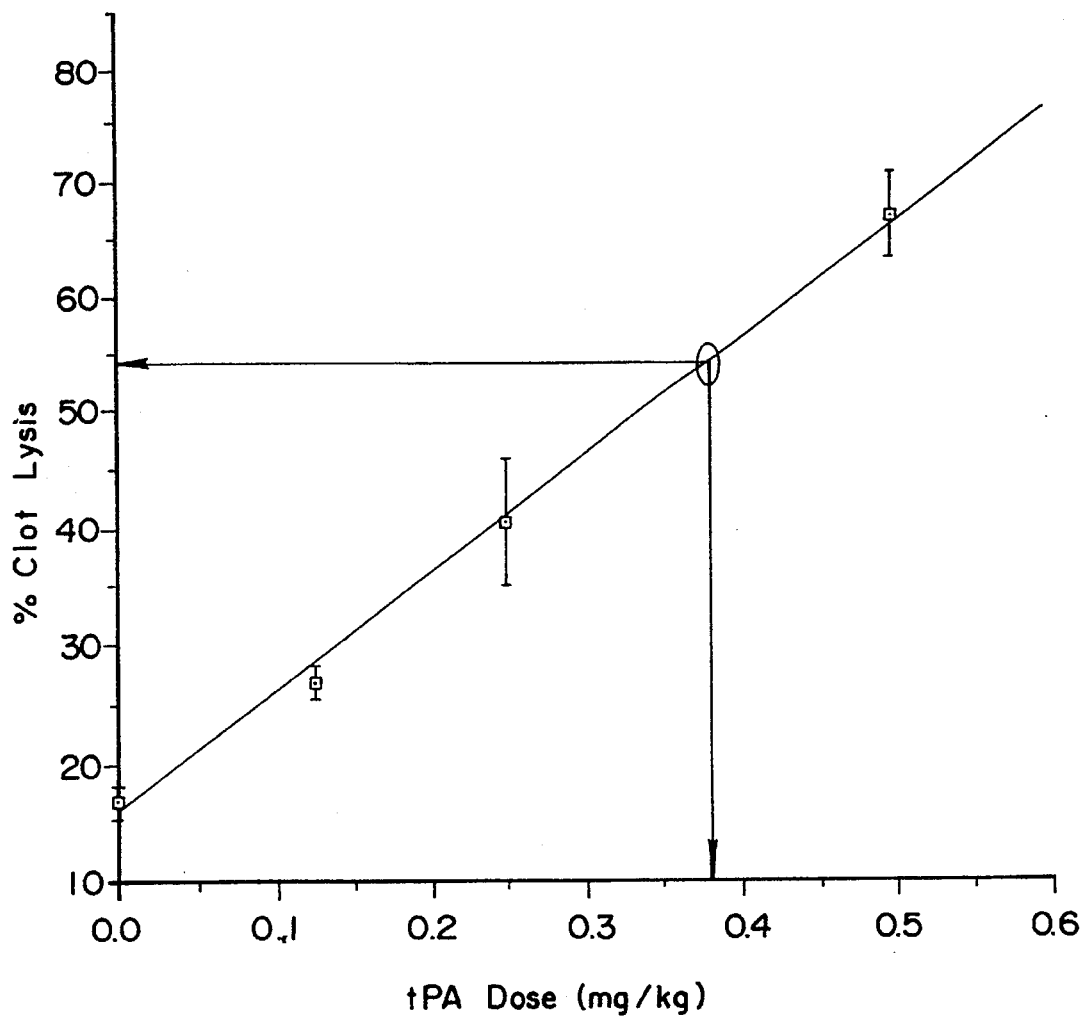
FIG. 2—tPA Standard Clot Lysis Curve 2 for Model II. Data represented as Clot Lysis Mean +/− SEM (N=4)

Clot lysis standard curves were performed for varying doses of tPA from C127 mouse cells (Invitron). Variations in procedures resulted in slightly different baseline clot lysis. To compare the data, standard curves were established for each procedure. These standard curves are shown in FIGS. 1 and 2. A linear dose dependency is observed with both sets of data. A comparison of the two sets of data reveals a lower background in standard curve 1 (FIG. 1): 8% vs. 17%. The chosen dose of tPA (0.125 mg/kg) for the peptide experiments gave 17% and 27% lysis, respectively, for the two sets of experiments. This dose was chosen as the baseline for the peptide study so that an increase in clot lysis would be observable. Increases in clot lysis were evaluated by two methods. In the first method, fold increases in % clot lysis were calculated as follows:

$$\frac{\% \text{ clot lysis (tPA + peptide)} - \% \text{ background lysis}}{\% \text{ clot lysis (tPA)} - \% \text{ background lysis}}$$

In the second method, the equivalent dose of tPA necessary to obtain the clot lysis observed with tPA and peptide was extrapolated from the appropriate standard curve. Fold increase in tPA dose was determined as follows:

$$\frac{\text{equivalent tPA dose}}{\text{tPA dose (0.125 mg/kg)}}$$

EXAMPLE 2

In vivo thrombolysis was carried out as described in Collen, D., Stassen, J. M. & Verstraete, M., *J. Clin. Invest.* 71:368 (1983). New Zealand White rabbits (LSR Industries, Ill.) were used instead of White Belgian Dendermond rabbits. The rabbits were anesthetized with a combination of ketamine hydroxide (25 mg/kg I.M.) and Innovar vet (0.02 mg/kg fentanyl, 1.0 mg/kg droperidol I.M.) from Allemed Vet Supply, Fenton, Mo., instead of Hypnom fentanyl.

An isolated clot was formed in the rabbit jugular vein using bovine thrombin (Calbiochem, San Diego, Calif.) and $^{125}$I fibrinogen (Amersham, Arlington Heights, Ill.). The enhancer peptides were injected into the isolated jugular vein along with thrombin and radiolabelled fibrinogen prior to clot formation. The volume of thrombin to thrombus size was found to be essential for reproduction of this model. A thrombus of 0.3 mL to 0.45 mL required one unit of bovine thrombin in a volume of 0.05 mL. When thrombus size is 0.5 mL to 0.65 mL one unit of bovine thrombin was used in a volume of 0.1 mL. Thrombus sizes smaller than 0.3 mL or larger than 0.65 mL were not used. A woolen thread was used to hold the clot in place. To make a homogeneous clot, formation of the thrombus occurred during the mixing of thrombin with whole blood and $^{125}$I tracer after the thread was introduced. After thrombus formation was complete, each animal received 500 units/kg heparin, administered subcutaneously. The thrombus was allowed to age 30 minutes prior to the start of infusion of tPA. Mouse C127 cell tPA (Invitron Lot #76-001-31395) was chosen as the control tPA for this study. This tPA (variable concentration) was infused over 4 hours at a rate of 6 mL/hr. Blood samples were taken every hour from the femoral vein, and clot lysis was measured by comparison of residual radioactivity in the clot at the end of 4 ½ hours.

Figure 3:
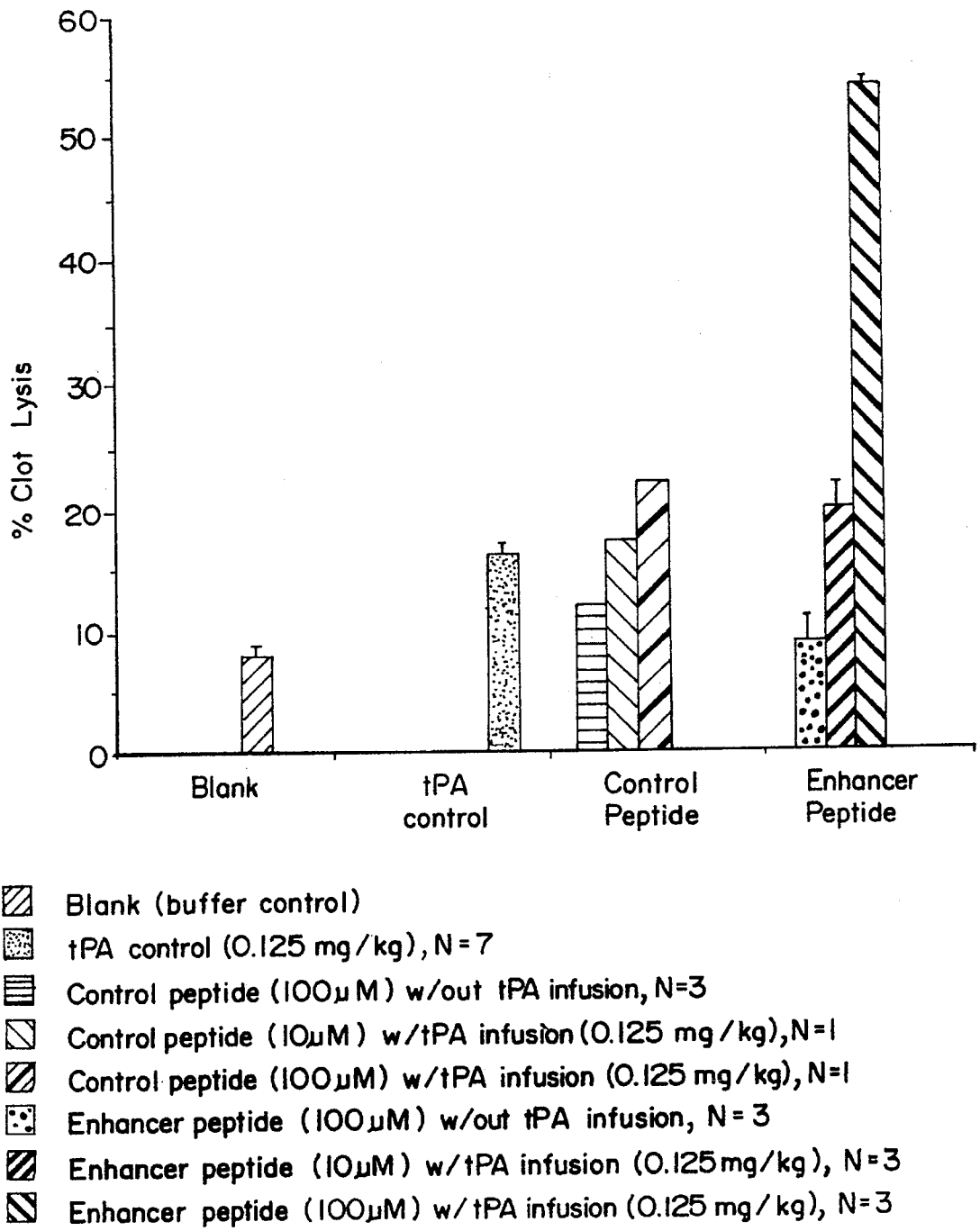
FIG. 3—Percent of clot lysis in rabbit model I.

FIG. 3 shows the results when two concentrations of peptides (enhancer peptide and control) were added during formation of the clot: 10 μM and 100 μM. After the clot formed, tPA (mouse C127, Invitron) was infused (6 mL/hr) for four hours. A nearly subthrombolytic dose of tPA is given in each peptide experiment (0.125 mg/Kg rabbit weight) to allow for increases in clot lysis with peptides. Blood samples were taken every hour during infusion and once 30 minutes after the infusion is discontinued. Clot lysis (0.125 mg/kg tPA) in this set of experiments was 16 +/- 1% and lysis comparisons should be made with standard curve 1 (FIG. 1). When peptide was present in the clot and tPA was infused, the enhancer peptide increased clot lysis significantly only at the 100 μM concentration in the clot. The amount of clot lysis observed with the enhancer peptide would require an infusion of approximately 0.8 mg/kg tPA or a 6.5 fold increase in tPA dose if administered as tPA alone (standard curve 1 FIG. 1 ).

Figure 4:
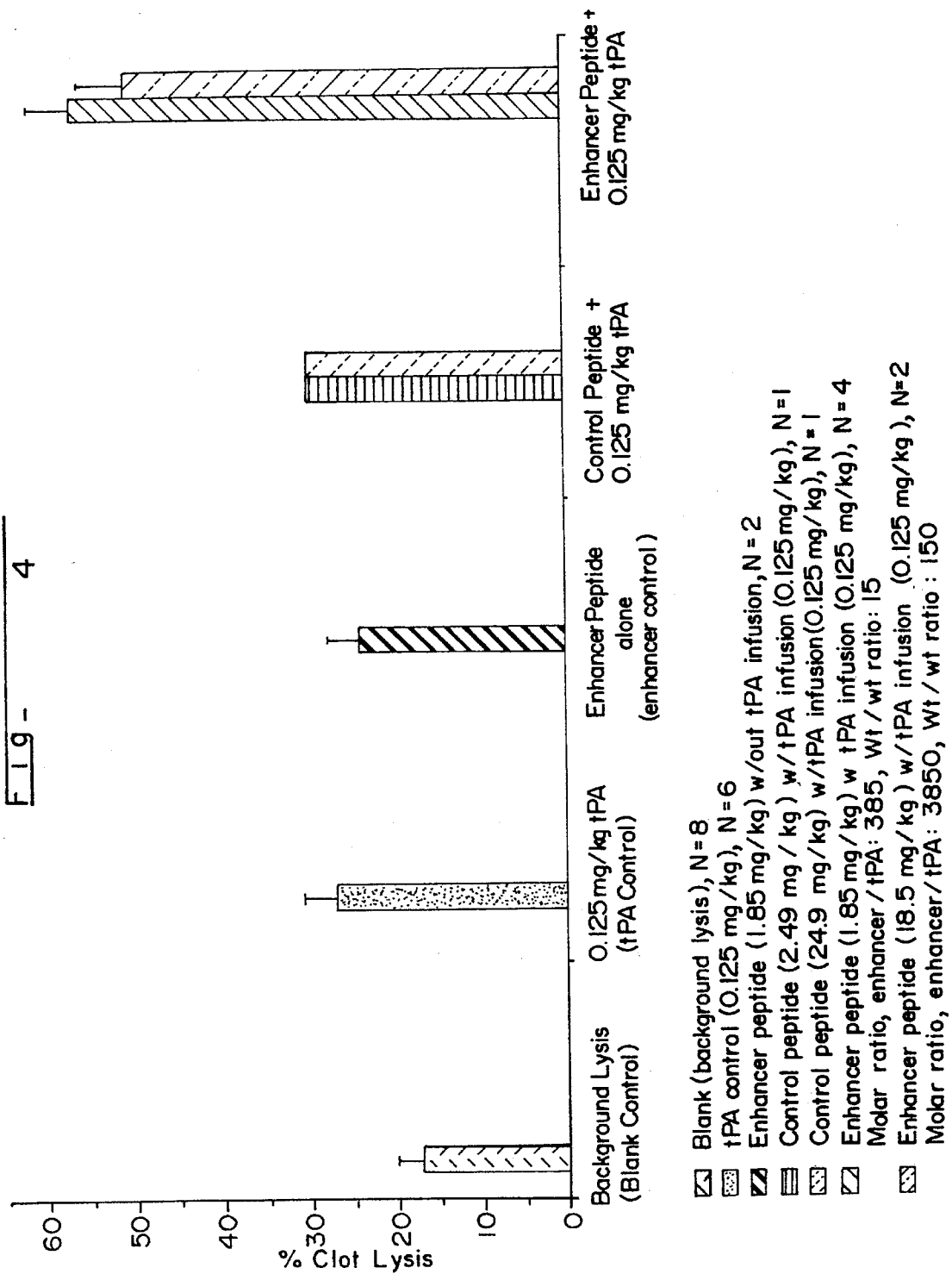
FIG. 4—Percent of clot lysis in rabbit model II.
Figure 5:
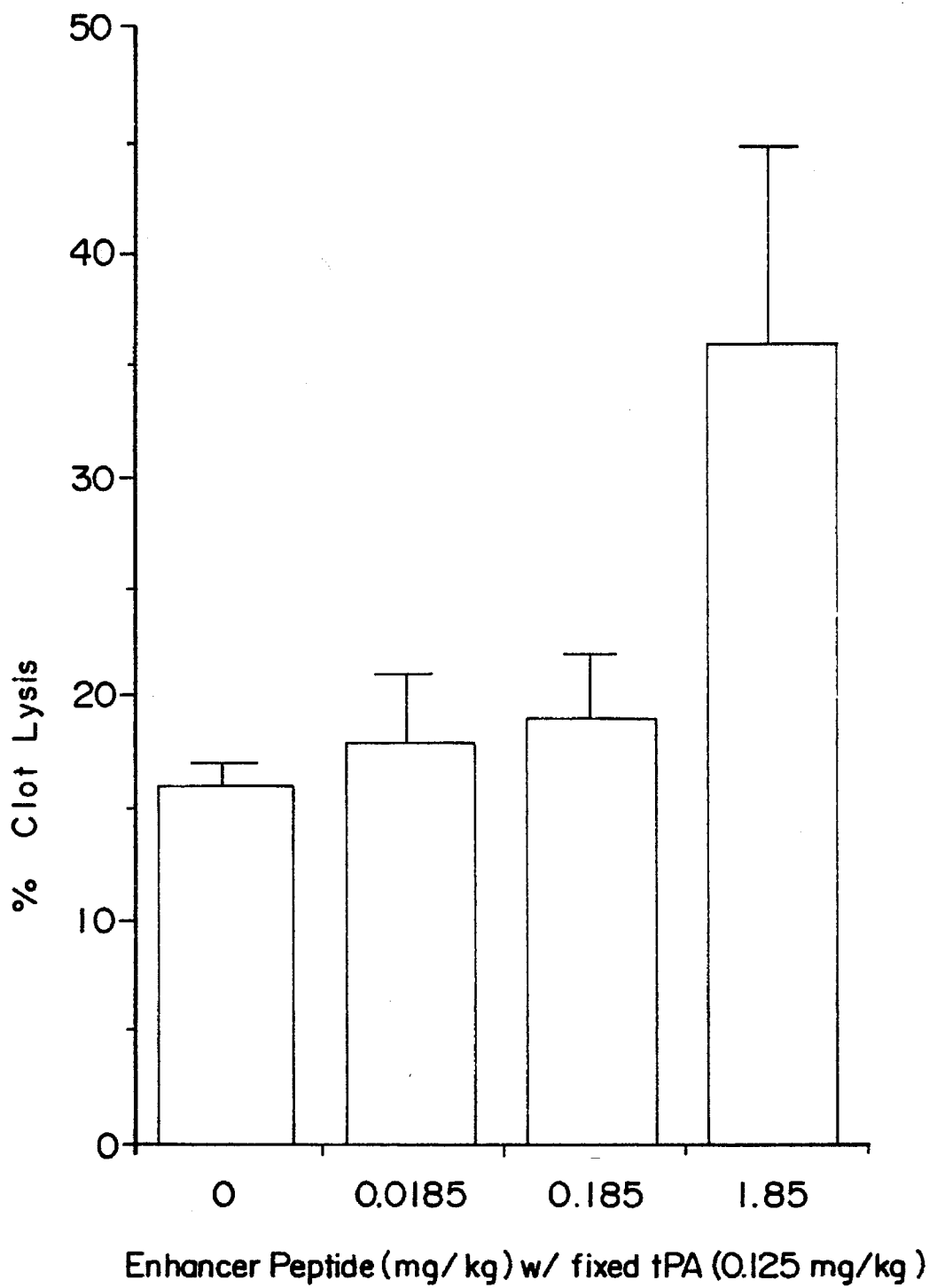
FIG. 5—Dose response of enhancer peptide. Data represented as mean +/− SEM (N=3 for each data point.) tPA dose =0.125 mg/kg.

A dose response study was performed with the peptides using a constant tPA dose (FIG. 5). Three doses are tested:

1.85 mg/kg, 0.185 mg/kg and 0.0185 mg/kg, which correspond to molar ratios of peptide to tPA of 385, 38.5, and 3.85, respectively with weight ratios of enhancer peptide to tPA of 15:1, 1.5:1, and 0.15:1 respectively. Peptides and tPA are infused as indicated in FIG. 4; however, the conditions of the experiments (background lysis) are as shown in standard curve 1 (FIG. 1). The enhancer peptide effect fell off drastically below 1.85 mg/kg (molar ratio of enhancer/tPA; 385 and weight ratio of 15). No significant increase in clot lysis was observed at lower enhancer peptide doses.

Fibrinogen and antiplasmin levels were monitored in each rabbit experiment in substantial accordance with the teaching of Example 1. Table I gives a summary of this data. Fibrinogen and α-2 antiplasmin levels did not change in any of the experiments, including rabbits which had increased clot lysis due to infusion of the enhancer peptide. Increased levels of systemic plasmin have been shown to deplete levels of fibrinogen as well as α-2 antiplasmin. These data indicate that systemic plasmin activation by tPA is minimal and that the fibrin specificity of tPA is not altered.

The tPA antigen levels were monitored hourly to determine if the increase in clot lysis is due to an extended tPA half-life. Enzyme linked immunosorbent assay (ELISA) data (see Table 1) indicates that tPA half-life is not being affected. Antigen levels of tPA decreased after infusion is stopped, indicating normal clearance of the exogenous tPA.

TABLE I

Effect of enhancer peptide on fibrinogen, α-2 antiplasmin and tPA antigen levels during rabbit clot lysis experiments.

| Enhancer Peptide dose (mg/kg) | Fibrinogen (% of baseline) | α-2 Antiplasmin (% of baseline) | tPA Antigen (mg/ml) During Infusion | tPA Antigen (mg/ml) 30 min. after Infusion |
| --- | --- | --- | --- | --- |
| 0 (tPA only) | 100 | 94 +/− 2 | 47 | 4 +/− 2 |
| 18.5 | 91 +/− 13 | ND | 49 +/− 13 | 9 +/− 2 |
| 9.25 | 91 | 92 +/− 2 | 24 | 3 |
| 1.85 | 100 +/− 1 | 86 +/− 8 | 33 +/− 9 | 5 +/− 2 |
| 0.185 | 100 +/− 1 | 96 +/− 1 | 26 +/− 1 | 0 |
| 0.0185 | 100 | 87 +/− 7 | 30 | 0 |

EXAMPLE 3

Enhancer peptides were dissolved in 1 mL water for injection (Abbott Labs, North Chicago, Ill.), and pH adjusted to 6–7 with pyrogen free NaOH (Sigma, St. Louis, Mo.). This solution was added to tPA (0.125 mg/Kg rabbit) dissolved in saline buffer containing 0.01% tween 80 in a total volume of 28 mL. Peptide and tPA were allowed to mix fifteen minutes prior to infusion. The timing of the experiment is such that the end of this time corresponded to the end of the 30 minute clot aging time. At this point, a 10% bolus was given within one minute. The rest of the solution was infused at a rate of 6 mL/hr over four hours. Blood samples were taken at hourly intervals, drawn in citrate. The final blood sample was drawn 30 minutes after the infusion is complete.

A dose response study was performed with the enhancer peptide using a constant tPA dose (FIG. 5 shows the results) in substantial accordance with the teaching of Example 2. The molar ratio of enhancer peptide to tPA was 385, 38.5 and 3.85. The wt/wt ratio of enhancer peptide/tPA was 15, 1.5 and 0.15. The control peptide alone did not effect clot lysis at these doses in agreement with the first model. Rabbits in which the enhancer peptide was infused along with tPA demonstrated significant increases in clot lysis. This is equivalent to the lysis achieved by a 3-fold increase in tPA dose (0.38 mg/kg tPA). See example 1 for calculations.

Peptide and tPA are infused as indicated in FIG. 4; however, the conditions of the experiments (background lysis) are as shown in standard curve 1 (FIG. 1). The enhancer peptide effect fell off drastically below 1.85 mg/kg (molar ratio of 385 and wt/wt ratio of 15 of enhancer peptide to tPA). No significant increase in clot lysis is observed at lower enhancer peptide doses.

Fibrinogen and α-2 antiplasmin levels were monitored in each rabbit experiment in substantial accordance with the teachings of Example 1. Table I gives a summary of this data. Fibrinogen and α-2 antiplasmin levels did not change in any of the experiments including rabbits which had increased clot lysis due to infusion of the enhancer peptide.

EXAMPLE 4

A series of experiments were performed to determine if an increase in clot lysis could be obtained when the enhancer peptide is infused along with tPA. The control peptide has the following sequence of amino acids:

Tyr—Lys—Leu—Gln—Arg—Gly—Leu—Val—Ile—Leu—
Val—Leu—Asp—Ser—Gly—Gly—Thr—Gln—Val—Phe—
Ile—Val—Thr—Lys—Leu—Asn—Gln—Gly—Thr—Ser—Lys.

This control peptide has a different primary sequence but is similar on the basis of functional equivalence as described by G. Glover et al., *Molec. Immunol.* 25:1261 (1988). These experiments were carried out in the same manner as those in standard curve 2 (FIG. 2). See Example 3. The results from this study are shown in FIG. 4. Rabbits in which the enhancer peptide is infused along with tPA demonstrated significant increases in clot lysis. Each dose of enhancer peptide increased jugular vein clot lysis from 27% (tPA control) to 57%. Substraction of 17% background lysis from each value suggests this is equivalent to the lysis achieved by a four-fold increase (40/10) in tPA dose (extrapolated from FIG. 2). Control Peptide did not effect clot lysis. The enhancer peptide was infused without tPA to determine if the mechanism of action was something other than action upon the exogenous tPA. Clot lysis did not increase significantly at the 1.85 mg/kg peptide dose (24 +/− 4). This agrees with data where peptide was applied directly to the clot (FIG. 3).

A dose response study was performed with the peptide using a constant tPA dose (FIG. 5) in substantial accordance with the teaching of Example 2. Peptides and tPA were infused as indicated in FIG. 4; however, the conditions of the experiments (background lysis) are as shown in standard curve 1 (FIG. 1). The enhancer peptide effect fell off drastically below 1.85 mg/kg. No significant increase in clot lysis is observed at lower doses.

Fibrinogen and antiplasmin levels were monitored in each rabbit experiment in substantial accordance with the teachings of Example 1. Table I gives a summary of this data. Fibrinogen and α-2 antiplasmin levels did not change in any of the experiments including rabbits which had increased clot lysis due to infusion of the enhancer peptide.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

What is claimed is:

1. A method for enhancing tPA mediated clot lysis which comprises administering a lysis enhancing amount of a peptide of the formula:

Ala—Gly—Arg—Ser—Leu—Asn—Pro—Asn—Arg—Val—Thr—Phe—Lys—Ala—Asn—Arg—Pro—Phe—Leu—Val—Phe—Ile, with a lysis effective amount of tissue plasminogen activator.

2. The method of claim 1 in which the peptide is administered between about one minute and thirty minutes prior to administration of tissue plasminogen activator.

3. The method of claim 1 in which the peptide is administered between about one minute and thirty minutes after the administration of tissue plasminogen activator.

4. The method of claim 1 in which the peptide is administered simultaneously with the administration of tissue plasminogen activator.

5. The method of claim 1 in which the lysis enhancing amount of the peptide is about 100 mg to 2250 mg.

6. The method of claim 2 in which the lysis enhancing amount of the peptide is about 100 mg to 2250 mg.

7. The method of claim 3 in which the lysis enhancing amount of the peptide is about 100 mg to 2250 mg.

8. The method of claim 4 in which the lysis enhancing amount of the peptide is about 100 mg to 2250 mg.

9. A method for enhancing tPA mediated clot lysis which comprises administering a lysis enhancing amount of a pharmaceutically-acceptable composition comprising a tPA mediated clot lysis enhancing amount of a peptide of the formula:

Ala-Gly-Arg-Ser-Leu-Asn-Pro-Asn-Arg-Val-Thr-Phe-Lys-Ala-Asn-Arg-Pro-Phe-Leu-Val-Phe-Ile, and a lysis effective amount of tissue plasminogen activator.

10. The method of claim 9 in which the composition has a ratio of peptide to tPA from about 20:1 to 1:5 parts by weight.

11. The method of claim 9 in which the composition has a ratio of peptide to tPA from about 15:1 to 1:1 parts by weight.

12. A pharmaceutically-acceptable composition comprising a tPA mediated clot lysis enhancing amount of a peptide of the formula:

Ala-Gly-Arg-Ser-Leu-Asn-Pro-Asn-Arg-Val-Thr-Phe-Lys-Ala-Asn-Arg-Pro-Phe-Leu-Val-Phe-Ile, and a lysis effective amount of tissue plasminogen activator.

13. The composition of claim 12 in which the ratio of peptide to tPA ranges from about 20:1 to 1:5 parts by weight.

14. The composition of claim 12 in which the ratio of peptide to tPA ranges from about 15:1 to 1:1 parts by weight.

* * * * *